US010765383B2

(12) United States Patent
Martens et al.

(10) Patent No.: US 10,765,383 B2
(45) Date of Patent: Sep. 8, 2020

(54) IMAGING WITH ENHANCED X-RAY RADIATION

(71) Applicant: KONINKLIJKE PHILIPS N.V., Eindhoven (NL)

(72) Inventors: Gerhard Martens, Henstedt-Ulzburg (DE); Ewald Roessl, Ellerau (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 228 days.

(21) Appl. No.: 15/743,304

(22) PCT Filed: Jul. 12, 2016

(86) PCT No.: PCT/EP2016/006458
§ 371 (c)(1),
(2) Date: Jan. 10, 2018

(87) PCT Pub. No.: WO2017/009302
PCT Pub. Date: Jan. 19, 2017

(65) Prior Publication Data
US 2018/0214093 A1    Aug. 2, 2018

(30) Foreign Application Priority Data

Jul. 14, 2015    (EP) ..................... 15176653

(51) Int. Cl.
*G21K 1/06*    (2006.01)
*A61B 6/06*    (2006.01)
(Continued)

(52) U.S. Cl.
CPC ............... *A61B 6/06* (2013.01); *A61B 6/40* (2013.01); *A61B 6/482* (2013.01); *G01N 23/044* (2018.02);
(Continued)

(58) Field of Classification Search
CPC .... G02B 5/10; A61B 6/06; A61B 6/40; A61B 6/482; G21K 1/02; G21K 1/067; G01N 23/20008; G01N 2223/316
See application file for complete search history.

(56) References Cited

U.S. PATENT DOCUMENTS 4,271,353 A * 6/1981 Ohtsuki ............. G01N 23/2076
378/70
4,969,175 A * 11/1990 Nelson ................... B82Y 10/00
378/146
(Continued)

FOREIGN PATENT DOCUMENTS

CA           824764      10/1969
DE          4130039       3/1993
(Continued)

OTHER PUBLICATIONS

Stern, et al., "Simple Method for focusing x rays using tapered capillaries", Applied Optics 27, 5135-5139 (1988).
(Continued)

*Primary Examiner* — David P Porta
*Assistant Examiner* — Djura Malevic
(74) *Attorney, Agent, or Firm* — Larry Liberchuk

(57) ABSTRACT

The invention relates to an X-ray imaging apparatus (2), comprising: a source (4) for generating X-ray radiation, an object receiving space (6) for arranging an object of interest for X-ray imaging, an X-ray collimator arrangement (8) arranged between the source (4) and the collimator arrangement (8), and an X-ray mirror arrangement (10). The mirror arrangement (10) comprises for example two tapered mirrors (22) facing each other and adapted for guiding X-ray radiation of the source (4) to the collimator arrangement (8). Consequently, the X-ray intensity at the object receiving space (6) is increased. In order to limit the X-ray radiation to an area, where the X-ray radiation can be utilized form (Continued)

imaging, an angle of spread Θm between the mirrors (22) and a length LM of each mirror (22) is adapted, such that a number of total reflections of X-ray radiation, provided by the source (4), at the mirrors (22) is limited. The limitation provides the effect that an angle of reflection Θr of the totally reflected X-ray radiation is limited. Consequently, an X-ray intensity at the object receiving space (6) is increased while constrains are provided, which prevent a large increase of a width of the X-ray radiation provided at the object receiving space (6), which effectively improves an imaging quality of an object of interest being arrangeable at the object receiving space (6).

15 Claims, 12 Drawing Sheets

(51) Int. Cl.
| | | |
|---|---|---|
| A61B 6/00 | (2006.01) | |
| G01N 23/044 | (2018.01) | |
| G01N 23/20008 | (2018.01) | |
| G02B 5/10 | (2006.01) | |
| G02B 27/09 | (2006.01) | |
| G21K 1/02 | (2006.01) | |

(52) U.S. Cl.
CPC ......... *G01N 23/20008* (2013.01); *G02B 5/10* (2013.01); *G02B 27/0927* (2013.01); *G02B 27/0983* (2013.01); *G21K 1/02* (2013.01); *G21K 1/067* (2013.01); *G01N 2223/316* (2013.01); *G21K 2201/064* (2013.01)

(56) References Cited

U.S. PATENT DOCUMENTS

| | | | |
|---|---|---|---|
| 5,001,737 A | 3/1991 | Lewis | |
| 5,077,774 A * | 12/1991 | Piestrup | G03F 7/70033 378/119 |
| 5,206,514 A * | 4/1993 | Brandner | G21K 4/00 250/484.4 |
| 5,261,970 A | 11/1993 | Landis | |
| 5,757,882 A * | 5/1998 | Gutman | B82Y 10/00 378/82 |
| 5,982,562 A | 11/1999 | Rode | |
| 6,278,764 B1 * | 8/2001 | Barbee, Jr. | B82Y 10/00 378/84 |
| 6,863,409 B2 * | 3/2005 | Cho | G01N 23/202 359/853 |
| 7,039,160 B2 * | 5/2006 | Hoheisel | A61B 6/06 378/84 |
| 7,330,535 B2 * | 2/2008 | Arenson | G21K 1/04 378/156 |
| 7,706,508 B2 * | 4/2010 | Arenson | G21K 1/04 250/233 |
| 7,978,822 B2 * | 7/2011 | Windt | A61B 6/4021 359/850 |
| 8,199,883 B2 * | 6/2012 | Arenson | G21K 1/04 378/156 |
| 8,447,012 B2 * | 5/2013 | Ichizawa | A61B 6/583 378/113 |
| 8,483,355 B2 * | 7/2013 | Ichizawa | G01N 23/16 378/53 |
| 8,488,744 B2 * | 7/2013 | Ichizawa | G01N 23/083 378/156 |
| 8,537,970 B2 * | 9/2013 | Bernhardt | A61B 6/4035 378/70 |
| 8,746,903 B2 * | 6/2014 | Bavdaz | G21K 1/06 359/850 |
| 8,824,631 B2 * | 9/2014 | Mitsuda | G21K 1/067 250/505.1 |
| 8,829,459 B2 * | 9/2014 | Ichizawa | G01N 23/16 250/375 |
| 9,057,962 B2 * | 6/2015 | Ceglio | G21K 1/067 |
| 2002/0070365 A1 * | 6/2002 | Karellas | A61B 6/06 250/581 |
| 2002/0080916 A1 * | 6/2002 | Jiang | B82Y 10/00 378/84 |
| 2004/0066903 A1 * | 4/2004 | Fujinawa | G01N 23/201 378/145 |
| 2004/0264644 A1 | 12/2004 | Goebel | |
| 2005/0058352 A1 * | 3/2005 | Deliwala | G01J 3/02 382/232 |
| 2007/0030947 A1 * | 2/2007 | Popescu | A61B 6/022 378/19 |
| 2007/0104320 A1 * | 5/2007 | Arenson | G21K 1/04 378/145 |
| 2007/0189444 A1 * | 8/2007 | Van Steven-Daal | A61B 6/032 378/6 |
| 2008/0013685 A1 * | 1/2008 | Iwasaki | B82Y 10/00 378/86 |
| 2009/0041198 A1 * | 2/2009 | Price | G21K 1/02 378/147 |
| 2009/0147922 A1 * | 6/2009 | Hopkins | B82Y 10/00 378/140 |
| 2009/0154650 A1 * | 6/2009 | Tanabe | A61N 5/1042 378/137 |
| 2009/0190720 A1 * | 7/2009 | Windt | A61B 6/4021 378/146 |
| 2011/0012014 A1 * | 1/2011 | Livne | A61B 6/032 250/252.1 |
| 2011/0122993 A1 * | 5/2011 | Ichizawa | G01N 23/083 378/51 |
| 2011/0147603 A1 * | 6/2011 | Ichizawa | G01N 23/16 250/375 |
| 2011/0206187 A1 * | 8/2011 | Lee | B82Y 10/00 378/122 |
| 2011/0242515 A1 * | 10/2011 | Ceglio | G02B 5/0891 355/67 |
| 2011/0253886 A1 * | 10/2011 | Hackenschmied | G01T 1/249 250/252.1 |
| 2012/0051499 A1 * | 3/2012 | Lee | A61B 6/032 378/16 |
| 2012/0269321 A1 * | 10/2012 | Behling | H01J 35/24 378/62 |
| 2013/0114795 A1 * | 5/2013 | Komoto | G21K 1/00 378/145 |
| 2014/0105370 A1 * | 4/2014 | Yamakawa | A61B 6/025 378/207 |
| 2018/0153486 A1 * | 6/2018 | Martens | A61B 6/4035 |
| 2018/0177475 A1 * | 6/2018 | Koehler | A61B 6/484 |

FOREIGN PATENT DOCUMENTS

| | | |
|---|---|---|
| JP | 2009250910 | 10/2009 |
| JP | 2011164043 A * | 8/2011 |
| JP | 2013057628 | 3/2013 |
| SU | 811327 | 3/1981 |
| WO | 2006068464 | 6/2006 |
| WO | 2009106291 | 9/2009 |
| WO | 2015/004934 | 1/2015 |

OTHER PUBLICATIONS

Aslund et al, "Physical characterization of a scanning photon counting digital mammography system based on Si-strip detectors" Med. Phys. 34, 1918-1925 (2007).

Guinier, "X-Ray Diffraction", Dover Publications, Inc, New York, (1994), Chapter 1, pp. 1-3.

James, "The optical principles of the diffraction of x-rays", Ox Bow Press, Woodbridge, Connecticut, (1948), p. 173.

Parratt; "Surface Studies of Solids by Total Reflection of X-Rays" Phys. Rev. 95, 359-369 (1954), Abstract.

(56) References Cited

OTHER PUBLICATIONS

Henke, "Ultrasoft-X-Ray Reflection, Refraction, and Production of Photoelectrons (100-1000-eV Region)" Phys. Rev. A6, 94-104 (1972))., Abstract.

Henke, et al., "X-Ray Interations: Photoabsorption, Scattering, Transmission and Reflection at E=50-30,000 eV, Z=1-92"; Atomic Data and Nuclear Data Tables 54, 181-342 (1993).

* cited by examiner

IMAGING WITH ENHANCED X-RAY RADIATION

CROSS REFERENCE TO RELATED APPLICATIONS

This application is the U.S. National Phase application under 35 U.S.C. § 371 of International Application No. PCT/EP2016/066458, filed Jul. 12, 2016, published as WO 2017/009302 on Jan. 19, 2017, which claims the benefit of European Patent Application Number 15176653.2 filed Jul. 14, 2015. These applications are hereby incorporated by reference herein.

FIELD OF THE INVENTION

The present invention relates to imaging of an object of interest with enhanced X-ray radiation, and relates in particular to an X-ray imaging apparatus and an X-ray imaging system.

BACKGROUND OF THE INVENTION

For X-ray imaging, and in particular for X-ray mammography or for X-ray tomosynthesis, the bremsstrahlung of an X-ray source is utilized. The lifetime and the reliability of an X-ray source often depend on the workload of the X-ray source, wherein the workload relates to the rate between the power of the generated X-ray radiation and the possible maximal power of the X-ray radiation. Different levels of X-ray radiation power may be required. For example, in particular X-ray mammography, a higher power level of the X-ray source may be needed when scanning women with larger and thicker breasts. Increasing the maximal power of an X-ray radiation source would, however, increase the costs of a respective X-ray apparatus or system. For example, DE 41 30 039 A1 relates to an arrangement of an X-ray source and a collimator for generating collimated X-ray radiation, which is guided from an exit of the collimator to an object receiving space. It has been shown that X-ray radiation utilization of the X-ray radiation generated by the X-ray source has an effect on lifetime and reliability of the X-ray source.

JP2009250910 A discloses a system for generation of highly monochromatic X-rays by means of Bragg reflection on crystals.

SUMMARY OF THE INVENTION

Thus, there is a need to provide enhanced X-ray radiation utilizable for imaging, increased lifetime and reliability, while keeping the costs at a moderate level.

The object of the present invention is solved by the subject-matter of the independent claims, wherein further embodiments are incorporated in the dependent claims. It should be noted that the following described aspects of the invention apply for the X-ray imaging apparatus and also for the X-ray imaging system.

According to a first aspect of the present invention, an X-ray imaging apparatus is provided, comprising a source for generating X-ray radiation emitting a polychromatic spectrum of x-ray energies, an object receiving space for arranging an object of interest for X-ray imaging, an X-ray collimator arrangement, and an X-ray mirror arrangement. The X-ray collimator arrangement comprises at least a pre-collimator arranged between the source and the object receiving space for providing collimated X-ray radiation to the object receiving space. Further, the X-ray mirror arrangement is arranged between the source and the pre-collimator. The X-ray mirror arrangement comprises a set of two mirrors for guiding X-ray radiation of the source by providing total reflection of the whole polychromatic spectrum of x-ray energies of a part of the X-ray radiation in order to deflect the part of the X-ray radiation towards the pre-collimator such that in the region of the object receiving space enhanced radiation is provided in form of unreflected primary X-ray radiation in combination with secondary X-ray radiation by total reflection. The mirrors of the set of two mirrors are facing one another with an angle of spread larger than zero, such that the set of mirrors providing an X-ray entrance having an entrance width and an X-ray exit having an exit width, which is smaller than the entrance width.

The pre-collimator relates to an optical element comprising at least one aperture, wherein each aperture can be formed as a slit.

The mirror can also be referred to as an X-ray mirror.

The term "total reflection" refers to a reflection of an X-ray radiation wave, which strikes a boundary of a medium at an angle smaller than a particular critical angle with respect to a plane level to the boundary. The critical angle is the angle of incidence below which the total internal reflection occurs.

In an example, the critical angel $\Theta c$ is defined as:

$$\Theta c \approx 1.6 * 10^{\wedge}(-3) * \rho^{\wedge}(0.5) * \lambda,$$

where $\rho$ [g/cm$^3$] relates to the density of the medium and $\lambda$ [Å] relates to the wavelength of the X-ray radiation wave.

The set of two mirrors can also be referred to as the set of mirrors.

The "object-receiving space" relates to a space designated for arranging the object of interest. The object-receiving space may comprise an object support arrangement, for example a pair of paddles to hold and (temporarily) fix a breast for X-ray examination (e.g. screening) purposes.

The angle of spread relates to an acute angle of the two mirrors of the set of mirrors. The acute angle preferably corresponds to a double of an angle between an inward surface line of one of the mirrors and a longitudinal axis of the set of mirrors.

The effect of total reflection is absolute as long as the incident angle of the x-rays is smaller than the critical angle for the energy of the x-rays. The larger the energy, the smaller the critical angle of total reflection. Nevertheless for all energies in the polychromatic spectrum emitted by the x-ray source total reflection will take place. Hence monochromaticity of the source is not required neither particularly desirable.

According to an exemplary embodiment, the primary X-ray radiation forms a primary beam cone (also referred to as "cone beam") between the source and the pre-collimator, wherein the mirrors of the set of mirrors so-to-speak abut outside on the primary beam cone, and the angle of spread corresponds to a cone angle of the primary beam cone with a maximum deviation to the cone angle of 10%. The cone angle relates to an acute angle of the cone. The acute angle preferably corresponds to a double of an angle between a surface line of the cone and a cone longitudinal axis.

The "deviation" relates to a deviation in a plane defined by the surface line of the primary beam cone and longitudinal axis of the primary beam cone.

According to an exemplary embodiment, a length LM of each mirror of the set of mirrors is arranged, such that the inequality LM≤LMmax=LW/($\Theta c2-\Theta m$) holds, wherein:

LW is the width of the exit of the set of mirrors, $\Theta c2$ is the critical angle of reflection at a mirror of the set of mirrors, and $\Theta m$ is the angle of spread of the mirrors of the set of mirrors.

The length of a mirror preferably relates to an extension of the mirror in a direction of the longitudinal axis of the respective set of mirrors or in a direction with an angle to the longitudinal axis corresponding to an angle between an inward surface of the mirror and this longitudinal axis. According to an exemplary embodiment, the exit of the set of mirrors abuts to an aperture of the pre-collimator.

According to an exemplary embodiment, each mirror of the sets of mirrors comprises a substrate with a coating layer for providing the total reflection. Between the coating layer and the substrate, a boundary is provided that is configured to reduce scatter radiation from incoming radiation that is not reflected but passes a mirror surface and enters the coating layer.

According to a second aspect of the invention, an X-ray imaging system is provided. The imaging system comprises an X-ray imaging apparatus according to one of the previously examples, a detector for detecting X-ray radiation passing the object receiving space of the apparatus, an imaging processing unit, and an imaging output unit. The imaging processing unit is configured to receive signals from the detector and to compute image data of an object of interest arrangeable in the object receiving space based on these signals, and the imaging output unit is configured to provide an image data for further purpose. According to an aspect of the invention, an X-ray imaging apparatus is provided, which enables enhanced intensity of the X-ray radiation provided in an object receiving space of the X-ray imaging. A higher intensity of the X-ray radiation at the object receiving space allows improving the imaging quality. The object receiving space should be applied with X-ray radiation of the X-ray source of the X-ray apparatus. However, a limitation with respect to the lateral extension of this X-ray radiation is needed. Otherwise, X-ray radiation may be applied to the object receiving space without improving the imaging quality, since detectors for detecting X-ray radiation usually have a limited lateral extension. In order to fulfill both objections, the X-ray imaging apparatus provides a collimator and a set of two mirrors. The collimator comprises an aperture and is provided between the source and the object receiving space. The collimator provides collimated X-ray radiation to the object receiving space. The set of mirrors is provided between the collimator and the source. The mirrors of the set of mirrors are tapered and being opened to the source. Between the aperture of the collimator and the source, an X-ray beam cone is formed, whereas the X-ray waves (i.e. X-ray radiation) of the X-ray beam cone pass the aperture unreflected. The inward surfaces of the mirrors of the set of mirrors are facing each other and border to the outer surface of the beam cone. This configuration reduces the number of reflections of X-ray beams, which impinge one of the mirrors with an angle of incidence other than zero and smaller than a critical angle of total reflection. Further, the length of each mirror of the set of mirrors is limited, such that preferably a maximum of one or two total reflections for the same X-ray beam occurs. This limits an increase of an angle of reflection of the reflected X-ray radiation with respect to a longitudinal axis of the set of mirrors and thus limits the lateral extension of the X-ray radiation applied to the object receiving space. The part of the X-ray radiation generated by the source and being reflected at the mirrors is called the secondary X-ray radiation. Contrary to Bragg reflection total reflection functions for all angles and energies for which the condition of total reflection is satisfied and guarantees that many energy components of the primary radiation will be subject to total reflection and thus be part of the secondary X-ray radiation. The method is thus effective in combination with a polychromatic x-ray spectrum. The secondary X-ray radiation superposes the primary X-ray radiation at the object receiving space, wherein the primary X-ray radiation is formed by the X-ray radiation generated by the source and passing the set of mirrors and the collimator unreflected. Therefore, the intensity of the X-ray radiation at the object receiving space is increased, while the lateral extension of the X-ray radiation at the object receiving space is limited. Accordingly, by using the same source, an increase of the imaging quality is achievable without increasing significantly a dose of X-ray radiation to an object of interest not effectively utilized for imaging. At the same time, a decrease in lifetime for the source is prevented, since the X-ray radiation provided by the source is utilized more efficiently.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
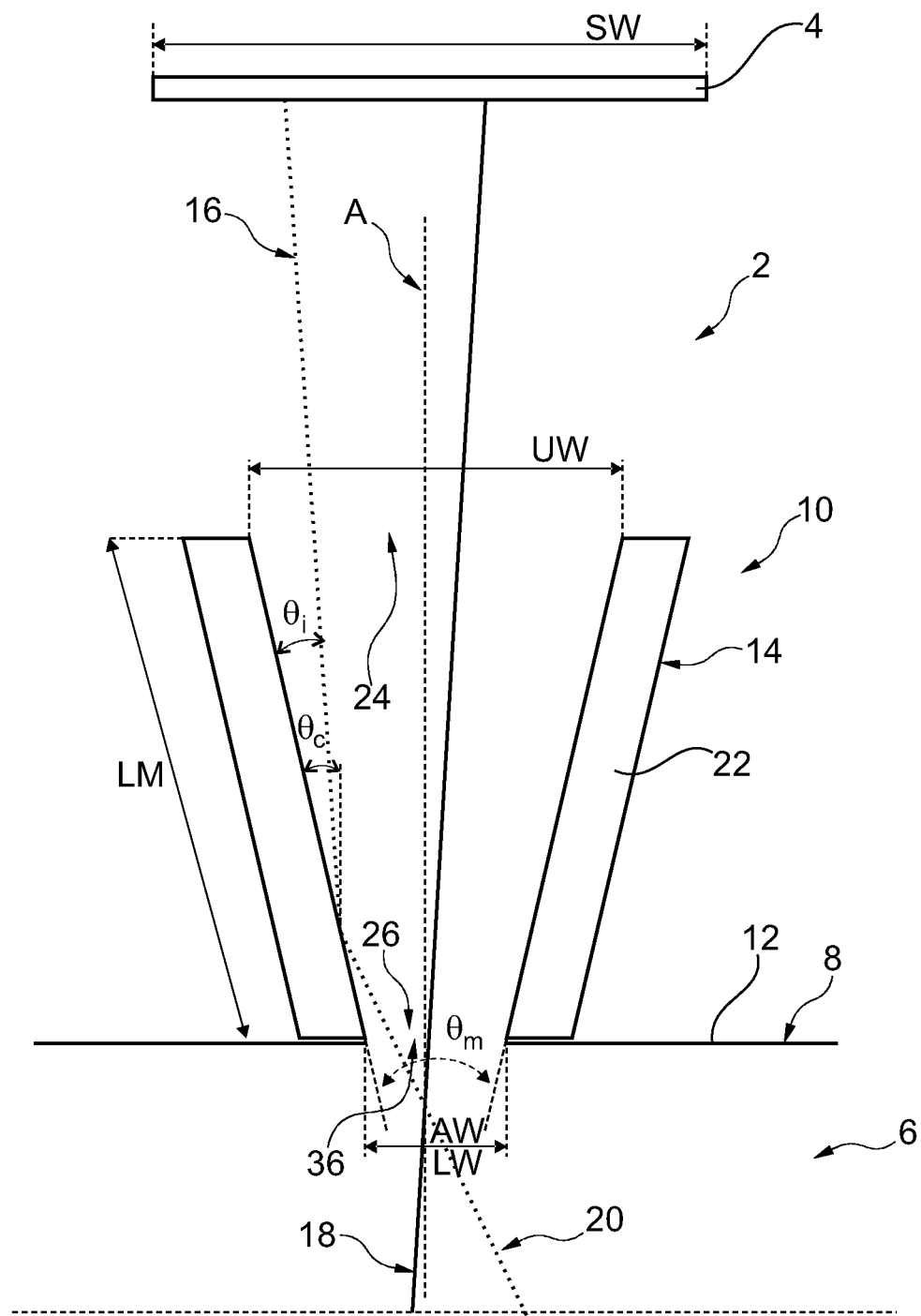
FIG. 1 shows a schematic setup of a first example of an X-ray imaging apparatus.

FIG. 1 shows an example of an X-ray imaging apparatus 2. The X-ray imaging apparatus 2 comprises a source 4 for generating X-ray radiation, an object receiving space 6 for arranging an object of interest for X-ray imaging, an X-ray collimator arrangement 8, and an X-ray mirror arrangement 10. The X-ray collimator arrangement 8 comprises at least a pre-collimator 12. The pre-collimator 12 is arranged between the source 4 and the object receiving space 6 for providing collimated X-ray radiation to the object receiving space 6. The X-ray mirror arrangement 10 is arranged between the source 4 and the pre-collimator 12. The X-ray mirror arrangement 10 comprises a set of two mirrors 14 for guiding X-ray radiation of the source 4 by providing a total reflection of a part 16 of the X-ray radiation in order to deflect the part 16 of the X-ray radiation towards the pre-collimator 12, such that, in the region of the object receiving space 6, enhanced radiation is provided in form of an unreflected primary X-ray radiation 18 in combination with a secondary X-ray radiation 20 by total reflection. The mirrors 22 of a set of mirrors 14 are facing one another with an angle of spread $\theta_m$ larger than zero, such that the set of mirrors 14 providing an X-ray entrance 24 having an entrance width UW and an (X-ray) exit 26 having an exit width LW, which is smaller than the entrance width UW.

The source 4 can also be referred as X-ray source. The source 4 is preferably of the kind, which is generally known in the state of the art. The source 4 is preferably provided as a rigid X-ray source unit, in particular such as the x-ray focus of a stationary or rotation anode x-ray tube or as a radio-active γ-emitter. It is to be noted that rigid attachments or mounting features are not further shown. In an example, the source 4 is the focus of an X-ray tube emitting a polychromatic (white) spectrum of x-ray energies. The source 4 is adapted for generating X-ray radiation. In particular, the X-ray radiation generated by the source 4 has energy between 20 keV and 40 keV. Preferably, the source 4 comprises a wavelength filter, which is adapted for suppressing or damping X-ray radiation having a wavelength corresponding to the energy of more than 20 keV.

The object receiving space 6 is adapted for arranging the object of interest for X-ray imaging. Thus, the object receiving space 6 relates to a space designated for arranging the object of interest. The object receiving space 6 may comprise an object support arrangement (not shown), for example a pair of pads to hold and temporarily fix a breast for X-ray examination purposes, in particular for screening purposes.

For the pre-collimator 12, collimators are provided of a kind that are generally known in the state of the art. For example, the pre-collimator 8 comprises a plate, in particular an X-ray absorbing plate, with at least one hole, which is adapted for being passed by X-ray radiation. Accordingly, an aperture 36 of the pre-collimator 12 can be formed by the hole. Further preferred, the aperture 36 is formed as a slit. The aperture 36 or the slit, respectively, are adapted for being passed by X-ray radiation. X-ray radiation passing the pre-collimator 12, and in particular the aperture 36 or a slit of the pre-collimator 12, reaches the object receiving space 6.

X-ray radiation of the source 4 directed to the pre-collimator 12, but not passing the pre-collimator 12 through an aperture 36 of the pre-collimator 12, will instead impinge on a surface of the pre-collimator 12. The X-ray radiation impinging this surface of the pre-collimator 12 will very likely not reach the object receiving space 6. Instead, this X-ray radiation will very likely be absorbed by the pre-collimator 12. Accordingly, the X-ray radiation usually has not a sufficient effect for being utilized for imaging an object of interest being arranged in the object receiving space 6.

In order to improve the utilization of the total available X-ray radiation emitted from the source 4 for imaging an object of interest being arranged in the object receiving space 6, the X-ray mirror arrangement 10 is provided and arranged between the source 4 in the pre-collimator 12. As mentioned above, the X-ray mirror arrangement 10 comprises at least one set of two mirrors 14. The set of mirrors 14 is also referred as the set of mirrors 14. The set of mirrors 14 has the purpose of guiding at least a part 16 of the X-ray radiation generated by the source 4 towards the pre-collimator 12. Without the mirrors, this part 16 of the X-ray radiation would impinge the surface of the pre-collimator 12 and would thus be absorbed by the pre-collimator 12 without a sufficient effect for being utilized for imaging an object of interest. Hence, the set of mirrors 14 is adapted for guiding a part 16 of the X-ray radiation generated by the source 4 to the pre-collimator 12 by providing total reflection of the part 16 of the X-ray radiation of the source 4 in order to deflect the part 16 of the X-ray radiation to the pre-collimator 12, in particular to the aperture 36 of the pre-collimator 12, such that, in the region of the object receiving space 6, enhanced radiation is provided.

Generally, in the object receiving space 6, the primary X-ray radiation 18 is provided, which passes the mirror arrangement 10 and the pre-collimator 12 unreflected. Further, the secondary X-ray radiation 20 is provided in the object receiving space 6, namely by being previously totally reflected at one of the mirrors 22 of the set of mirrors 14 of the mirror arrangement 10. Accordingly, the part 16 of the X-ray radiation of the source 4 being totally reflected at one of the mirrors 22 forms the secondary X-ray radiation 20 in the object receiving space 6. The primary X-ray radiation 18 and the secondary X-ray radiation 20 are superposed in the object receiving space 6 and thus increase the intensity of the X-ray radiation provided to the object receiving space 6.

As a result, higher intensity of the X-ray radiation in the object receiving space increases the imaging quality. Alternatively, the output of the source 4 can be reduced without decreasing the imaging quality, while increasing the lifetime of the source 4.

Furthermore, a higher intensity of the X-ray radiation in the object receiving space allows a reduction of a measurement time for imaging an object of interest.

Each of the mirrors 22 of the set of mirrors 14 is adapted for totally reflecting X-ray radiation. Accordingly, each of the mirrors 22 can also be referred to as X-ray mirror.

The mirrors 22 preferably relate each to a plate with a suitable low atomic number mirror material, in particular with a atomic number lower than nine. The mirrors 22 further preferably relate each to a plate of a glass-ceramic. As an example, each mirror 22 can comprise a lithium aluminosilicate glass-ceramic. A mirror of that kind may have a specific density of 2.53. However, this is just one example for the specific density. Generally, a wide range of possible specific densities for the X-ray mirrors 22 is possible. Basically, total reflection occurs at the mirror 22 in case the mirror 22 has, with respect to the X-ray radiation, an optically thinner medium at a boundary surface to the space between the source 4 and the mirror 22. Since refractive indices in the X-ray radiation regime are smaller than 1, an X-ray total reflection can be observed upon grazing incidents on any material given the incidence occurs within the critical angle of incidence $\theta_c$. A simplified critical angle of incidence can be calculated as follows: $\theta_c = 1.6 \times 10^{-3} \times (\rho)^{-0.5} \times \lambda$, wherein ρ being the density in the units of g/cm$^3$ and λ denotes the X-ray wavelength in Å. The critical angle of incidence $\theta_c$ is typically in the order of a few mrad (milli-rad). For example, the critical angle of total reflections may be between 0.5 mrad and 2 mrad. In order to achieve total reflection with larger angles, the density of the material being used has to be increased, or metallic coating can be used, for example with silver or gold. In order to achieve total reflection with smaller angles, the density of the material being used for a mirror has to be decreased. For example, each mirror may comprises at least one plastic mirror layer, preferably having low atomic number elements.

When using such mirrors for the set of mirrors 14, an enhancement in radiation in the object receiving space 6 is made possible. The term total reflection refers to a reflection of the X-ray radiation wave being provided from the source 4, when the respective X-ray radiation wave strikes a boundary of the mirror 22 at an angle smaller than the critical angle with respect to a plain level of the boundary.

In order to increase the radiation in the object receiving space by combining the primary X-ray radiation 18 and the secondary X-ray radiation 20, the mirrors 22 of the set of mirrors 14 are facing one another with an angle of spread $\theta_m$ larger than zero. Accordingly, the set of mirrors 14 provides an X-ray entrance 24 having an entrance width UW for entering X-ray radiation of the source 4. In order to provide X-ray radiation to the object receiving space 6, the set of mirrors 14 provides the X-ray exit 26 with the exit width LW, which is smaller than the entrance width UW. A part of the X-ray radiation of the source 4 may pass the set of mirrors 14 unreflected, in order to form the primary X-ray radiation in the object receiving space 6. Another part 16 of the X-ray radiation of the source 4 impinges on at least one of the mirrors 22 with an incidence angle $\theta_i$ with respect to the plain level of the boundary surface of the mirror 22 smaller than the critical angle $\theta_c$, such that total reflection occurs. The X-ray radiation totally reflected leaves the set of mirrors 14, at least in part, through the X-ray exit 26, in order to form the secondary radiation 22.

Since the X-ray imaging apparatus 2 is adapted for providing a combination of the primary X-ray radiation 18 and the secondary X-ray radiation 20 in the object receiving space 6, an increase of a total flux of the X-ray radiation is provided in the object receiving space 6. It is to be noted, that the increase is caused by the tapered arrangement of the mirrors 22 of the set of mirrors 14 and its arrangement between the source 4 and the pre-collimator 12. Consequently, the X-ray imaging apparatus 2 is a cost efficient improvement for increasing the intensity of the X-ray radiation usable for imaging of an object of interest in the object receiving space 6. Further, the source 4 is not necessarily being operated at its power limits for providing sufficient flux in case larger or thicker objects of interest are arranged in the object receiving space 6 for imaging. Instead, the mirror arrangement 10 allows using the same source 4 for generating a sufficient X-ray radiation flux. Consequently, the lifetime of the source 4 increases and reduced costs for a premature source replacement are provided. Furthermore, the imaging quality may be increased in case of thick objects of interest to be placed at the object receiving space 6 for imaging, since the intensity of the enhanced X-ray radiation may be sufficient for screening such an object of interest. In case the X-ray imaging apparatus is used for mammography or tomosynthesis, scanning times for women can be improved, in particular reduced.

In an example, the pre-collimator 12 comprises a plate with an aperture 36. The plate of the pre-collimator 12 is preferably adapted for absorbing X-ray radiation, in particular for absorbing X-ray radiation provided by the source 4. In order for providing an enhanced X-ray radiation with the pre-collimator 12 to the object receiving space 6, the mirrors 22 of the set of mirrors 14 are preferably tapered, such that a part 16 of the X-ray radiation generated by the source 4 is totally reflected and thereby focused to the aperture 36 of the pre-collimator 12. In an example, the exit 26 of the set of mirrors 14 is aligned with the aperture 36 of the pre-collimator 12. Accordingly, the X-ray radiation totally reflected by one of the mirrors 22 may be reflected to the exit 26 of the set of mirrors 14, and thus, being reflected to the aperture 36 of the pre-collimator 12. In case the aperture 36 of the pre-collimator 12 and the exit 26 of the set of mirrors 14 are aligned, the reflected X-ray radiation can pass the aperture 36 and consequently provide the secondary X-ray radiation to the object receiving space 6. Further, the set of mirrors 14 and the aperture 36 of the pre-collimator 12 are preferably coaxially aligned with respect to a common longitudinal axis.

In an example, the aperture 36 of the pre-collimator 12 is arranged as a slit. Accordingly, the pre-collimator 12 may be referred to as a slit pre-collimator.

In an example, the mirrors 22 of the set of mirrors 14 are each arranged as planar mirrors having planar mirror surfaces. In particular, the surfaces are polished. According to an alternative example, the mirrors 22 of the set of mirrors 14 are arranged as curved mirrors 22, preferably each comprising a curved mirror surface. The surfaces are preferably polished.

In a further example, the mirrors 22 of the set of mirrors 14 are preferably mirror-segments of one common mirror.

In an example, a source width SW of the source 4 is larger than the entrance width UW of the entrance 24 of the set of mirrors 14. This increases the enhancement of the X-ray radiation provided in the object receiving space 6, since the mirrors 22 of the set of mirrors 14 can reflect a part 16 of the X-ray radiation of the source 4 at their total length LM.

In a further example, the exit width LW is smaller than the entrance width UW of the set of mirrors 14. According to a further example, the source width SW of the source 4 is larger than the exit width LW of the exit 26 of the set of mirrors 24. It is further preferred that a width AW of the aperture 36 corresponds to the exit width LW of the exit 26 of the set of mirrors 14. Alternatively, it is preferred that the width AW of the aperture 36 of the pre-collimator 12 is smaller than the exit width LW of the exit 26. According to a further example, the source width SW of the source 4 is larger than an aperture width AW of the aperture 36 of the pre-collimator 12.

Figure 2:
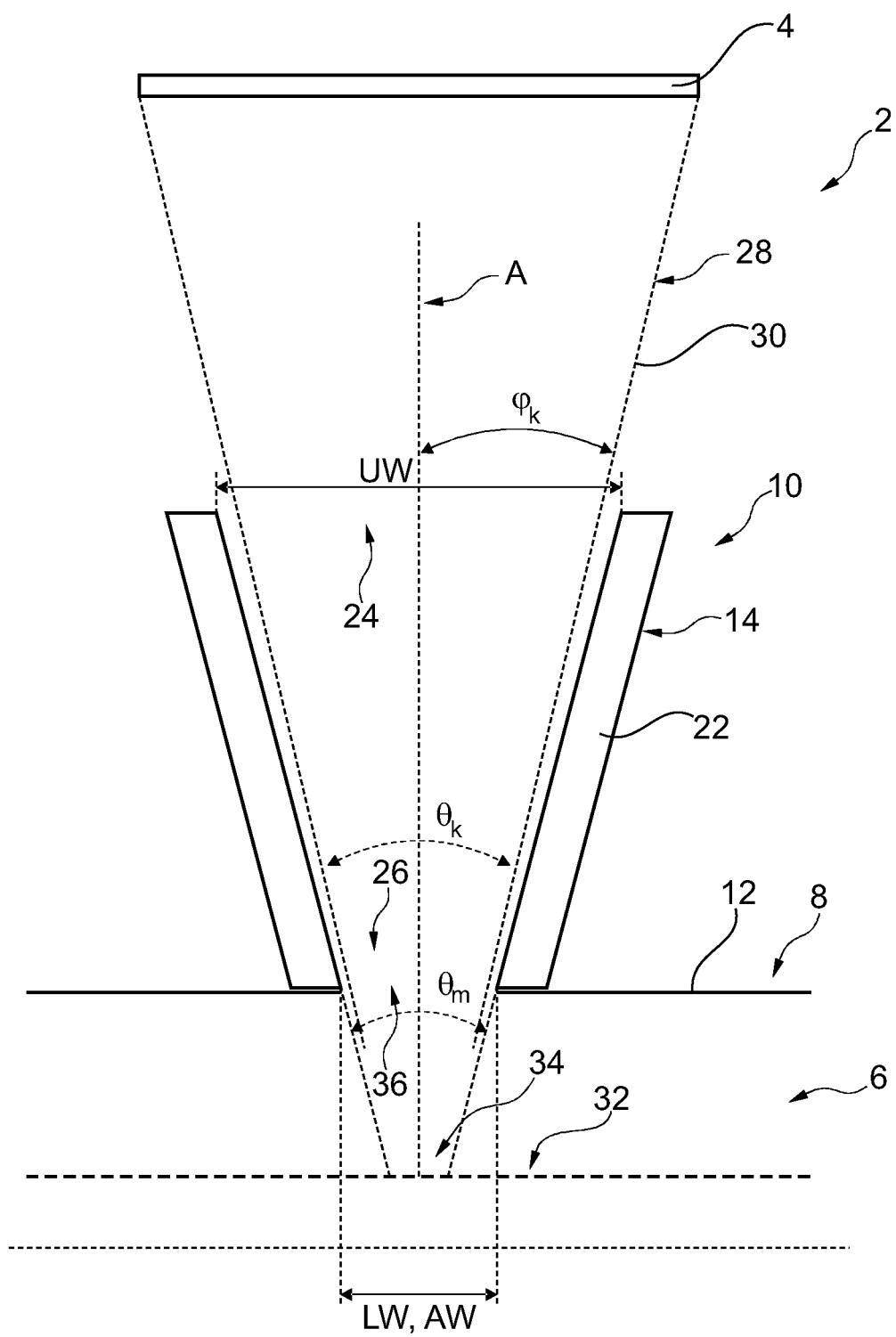
FIG. 2 shows a further example of an X-ray imaging apparatus.

FIG. 2 shows an example of the X-ray imaging apparatus 2, comprising the source 4, the object receiving space 6, the pre-collimator 12, arranged between the object receiving space 6 and the source 4, and the set of mirrors 14, which is arranged between the pre-collimator 12 and the source 4. The set of mirrors 14 comprises two mirrors 22, which are tapered, such that the entrance width UW of the entrance 24 of the set of mirrors 14 is larger than the exit width LW of the exit 26 of the set of mirrors 14. The exit 26 of the set of mirrors 14 is preferably aligned with an aperture 36 of the pre-collimator 12 with respect to a common longitudinal axis A. Accordingly, the X-ray radiation passing the set of mirrors 14 and the pre-collimator 12 unreflected will provide a primary X-ray radiation 18 to the object receiving space 6.

According to a further example, exemplary shown in FIG. 2, the primary X-ray radiation will form a primary beam cone 28 between the source 4 and the pre-collimator 12. Preferably, a width of the primary beam cone 28 is defined at one end by the width SW of the source 4 and at the other end by the width AW of the aperture 36 of the pre-collimator 12. Preferably, the mirrors 22 of the set of mirrors 14 abut to the outside on the primary beam cone 28. Accordingly, the angle of spread $\theta_m$ preferably corresponds to a cone angle $\theta_k$ of the primary beam cone 28 with a maximum deviation to the cone angle $\theta_k$ of 10%. The cone angle $\theta_k$ relates to an acute angle of the primary beam cone 28, which corresponds to a double of an angle $\varphi_k$ between a surface line 30 of the primary beam cone 28 and a longitudinal axis of the primary beam cone 28. Preferably, the cone longitudinal axis corresponds to the common longitudinal axis A of the set of mirrors 14 and the aperture 36 of the pre-collimator 12. In an example, the mirrors 22 of the set of mirrors 14 directly abut to the outside surface of the primary beam cone 28. In this case, the angle of spread $\theta_m$ of the mirrors 22 of the set of mirrors 14 and the cone angle $\theta_k$ of the primary beam cone 28 correspond exactly to each other. In case the angle of spread $\theta_m$ of the mirrors 22 of the set of mirrors 14 is larger or smaller than the cone angle $\theta_k$, the mirrors 22 abuts preferably at least partly at the outside surface of the primary beam cone 28. The deviation between the cone angle $\theta_k$ and the angle of spread $\theta_m$ is preferably limited to 10%. By limiting this deviation, a large decrease of lateral resolution of the X-ray radiation provided at the object receiving space 6 is prohibited.

In an example, the X-ray imaging apparatus 2 comprises a detector plane 32 for arranging a detector (not shown). Preferably, the mirror arrangement 8 and the collimator arrangement 10 are arranged between the source 4 and the detector plane 32.

Figure 3:
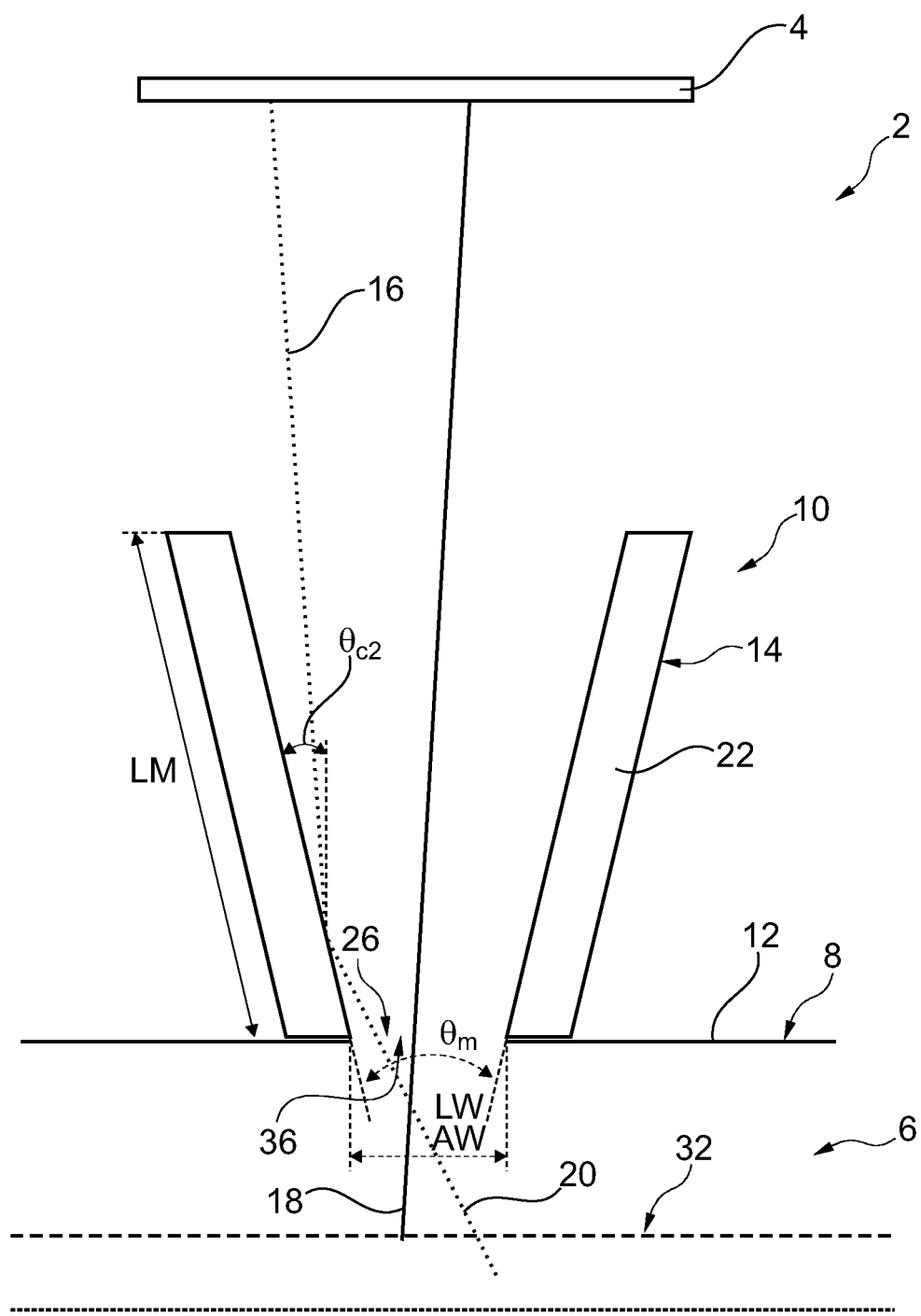
FIG. 3 shows a another example of an X-ray imaging apparatus.

According to a further example shown in FIG. 3, the X-ray imaging apparatus 2 is provided with the mirror arrangement 10 comprising at least one of the set of mirrors 14, wherein a length LM of each mirror 22 of the set of mirrors 14 is arranged, such that the image quality LM≤$LM_{max}$=LW/($\theta_{c2}-\theta_m$) holds, wherein LW relates to the width of the exit 26 of the set of mirrors 14, $\theta_{c2}$ relates to the critical angle of reflection at the mirrors 22 of the set of mirrors 14, and $\theta_m$ relates to the angle spread of the mirrors 22 of the set of mirrors 14. Limiting the length LM of each of the mirrors 22 of the set of mirrors 14 has the effect that a number of reflections of the X-ray radiation provided by the source 4 are limited, in particular to a second or first order reflection within the set of mirrors 14. It is to be noted, that a reflection angle $\theta_r$ of an X-ray beam of the X-ray radiation reflected by the mirrors 22 of the set of mirrors 14 with respect to a common longitudinal axis A of the set of mirrors 14 increases with each reflection at a mirror 22 of the set of mirrors 14. Accordingly, second order reflected X-ray beams, or an even higher order reflected X-ray beam, may pass the exit 26 of the set of mirrors 14, the aperture 36 of the pre-collimator 12 and the object receiving space 6 without being picked up by a detector which is arrangeable at the detector plane 32. A detector usually has a limited width for detecting X-ray radiation. Since a second order or an even higher order reflected X-ray beam has a higher reflection angle $\theta_r$, the respective X-ray beam may pass over the detector at the detector plane 32 and impinges at the detector plane 32 at a position, where the detector may not be arranged at. Accordingly, these X-ray beams would add an X-ray dose to an object of interest, in particular to a patient, without increasing the image quality. Since the above example shows a limitation for the length LM of the mirrors 22 of the set of mirrors 14, which provides a significant reduction of second order or higher reflected X-ray radiation beams at the mirrors 22 of the set of mirrors 14, the X-ray dose not utilized for the image quality is significantly reduced.

In an example, the length LM of each mirror 22 of the set of mirrors 14 is between 0.8×$LM_{max}$ and 1.2×$LM_{max}$, in particular between 0.9×$LM_{max}$ and 1.0×$LM_{max}$. As previously explained, the arrangement for the length LM of each mirror 22 of the set of mirrors 14 provide a very good reduction of second order or higher order reflections of X-ray radiation beams within the set of mirrors 14. Thus, by limiting the length LM close to the length $LM_{max}$ a technical effect as described above is provided at least similarly.

In an example, the critical angle of reflection $\theta_{c2}$ is defined as $\theta_{c2}=1.6\times10^{-3}\times\rho^{(0.5)}\times\lambda$, wherein $\rho$ [g/cm$^3$] relates to the density of the mirrors and $\lambda$ [Å] relates to the wavelength of the X-ray radiation.

In a further example, the X-ray radiation of the source 4 is filtered, such that the primary X-ray radiation and the part of the X-ray radiation being reflected at the set of mirrors 14 have an energy within an energy-bandwidth between 20 keV and 40 keV, in particular between 25 keV and 35 keV. At an energy of 25 keV, the wavelength of the X-ray radiation is about $\lambda$=0.5 Å. A preferred material for the mirrors 22 of the set of mirrors 14 is lithium aluminosilicate which preferably has a density of about $\rho$=2.53 g/cm$^3$. According to a further example, in particular shown in any of the preceding FIGS. 1 to 3, the exit 26 of the set of mirrors 14 abuts to the aperture 36 of the pre-collimator 12. Preferably, an end of the set of mirrors 14 facing the pre-collimator 12 directly abuts to a surface of the pre-collimator facing the set of mirrors 14. Further, preferably, the exit 26 of the set of mirrors 14 borders on to a rim of the aperture 36, in particular formed by the pre-collimator 12.

In a further example, the exit width LW of the exit 26 of the set of mirrors 14 corresponds to an aperture width AW of the aperture 36 of the pre-collimator 12. As exemplarily pointed out previously, the exit 26 of the set of mirrors 14 and the aperture 36 of the pre-collimator 12 are preferably aligned to a common longitudinal axis A. In case the exit 26 and the aperture 36 have corresponding widths, namely the exit width LW and aperture width AW, respectively, it is very likely, that X-ray radiation passing the exit 26 will also pass the aperture 36.

Figure 4:
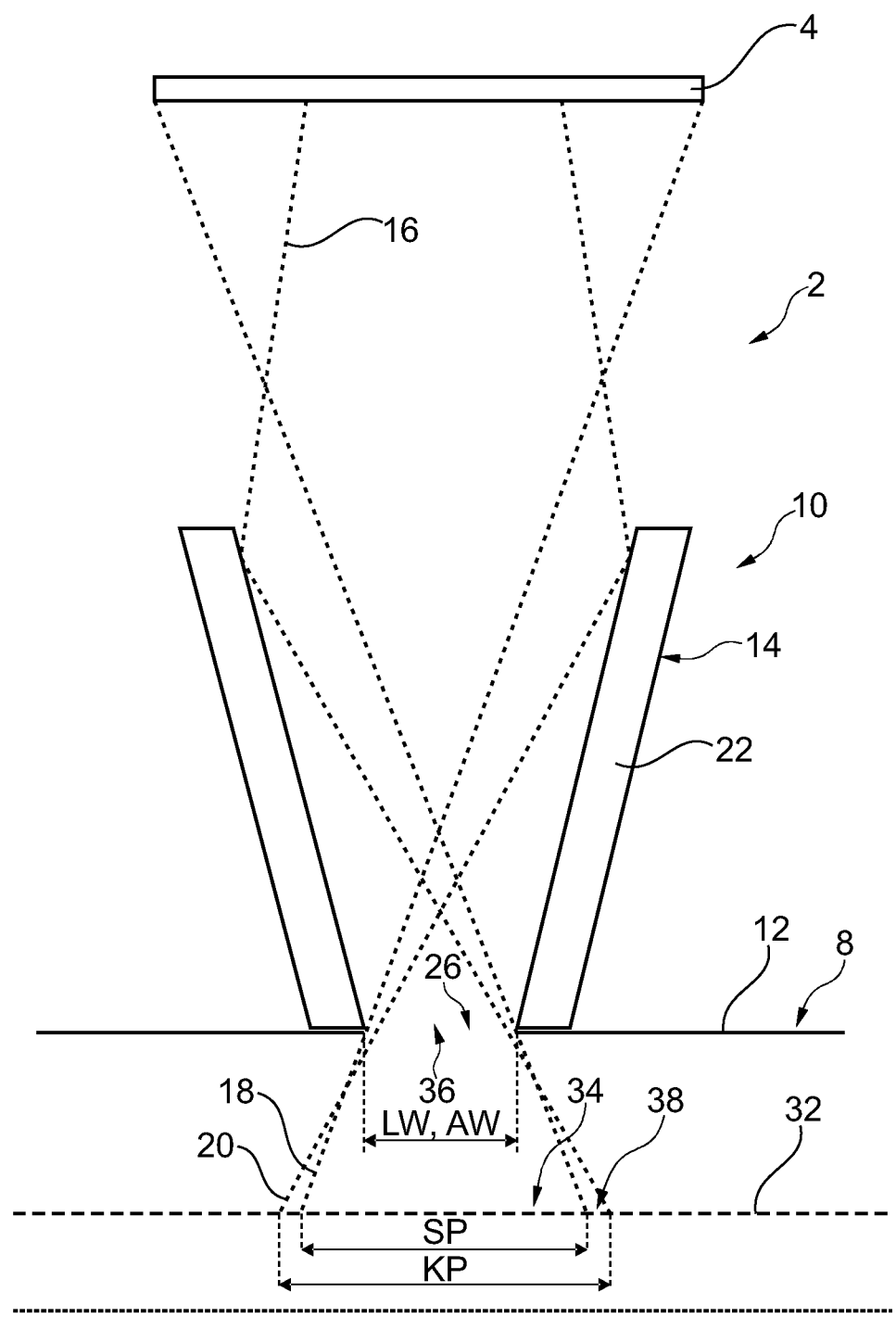
FIG. 4 shows a still further example of an X-ray imaging apparatus.

FIG. 4 shows a further example of the X-ray imaging apparatus 2 with respect to the primary X-ray radiation 18 and the secondary X-ray radiation 20. The primary X-ray radiation 18 passes the mirror arrangement 14 and the collimator arrangement 8 unreflected and thus creates a primary spot 34 at the detector plane 32. The primary spot 34 preferably relates to the area at the detector plane 32, where at least 75%, in particular at least 85%, of the unreflected X-ray radiation with respect to its distribution reaches the detector plane 32. According to a further example, exemplarily shown in FIG. 4, a secondary spot 38 at the detector plane 32 is created by the secondary X-ray radiation 20, which has been previously totally reflected at one of the mirrors 22 of the set of mirrors 14. The secondary spot 38 preferably relates to the area at the detector plane 32, where at least 75%, in particular at least 85%, of the reflected X-ray radiation with respect to its distribution reaches the detector plane 32.

In an example, a spot width KP of the secondary spot 38 is larger than a spot width SP of the primary spot 34. Preferably, the secondary spot 38 and the primary spot 34, each at the detector plane 32, are overlapping each other. Accordingly, an enhanced X-ray radiation is provided in the object receiving space 6.

In a further example, the spot width KP of the secondary spot 38 is larger than the aperture width AW of the aperture 36 of the pre-collimator 12 or as the exit width LW of the exit 26 of the set of mirrors 14. A spot width SP of the primary spot 34 is preferably larger than the aperture width AW of the aperture 36 of the pre-collimator 12 or the exit width LW of the exit 26 of the set of mirrors 24.

In an example, the spot width KP of the secondary spot 38 is in the range between 1.05×S and 1.5×S, where S relates to the amount of the spot width SP of the primary spot 34. This provides a large overlap between the primary spot 34 and the secondary spot 38, which helps increasing the intensity of the X-ray radiation in the object receiving space 6 and thus the utilization of the X-ray radiation for imaging an object of interest.

According to a further example, the mirror arrangement 10, and in particular the length LM of each mirror 22 of the set of mirrors 14, are arranged, such that at least 50% of the secondary X-ray radiation 20 impinges at the primary spot 34 at the detector plane 32.

Figure 5:
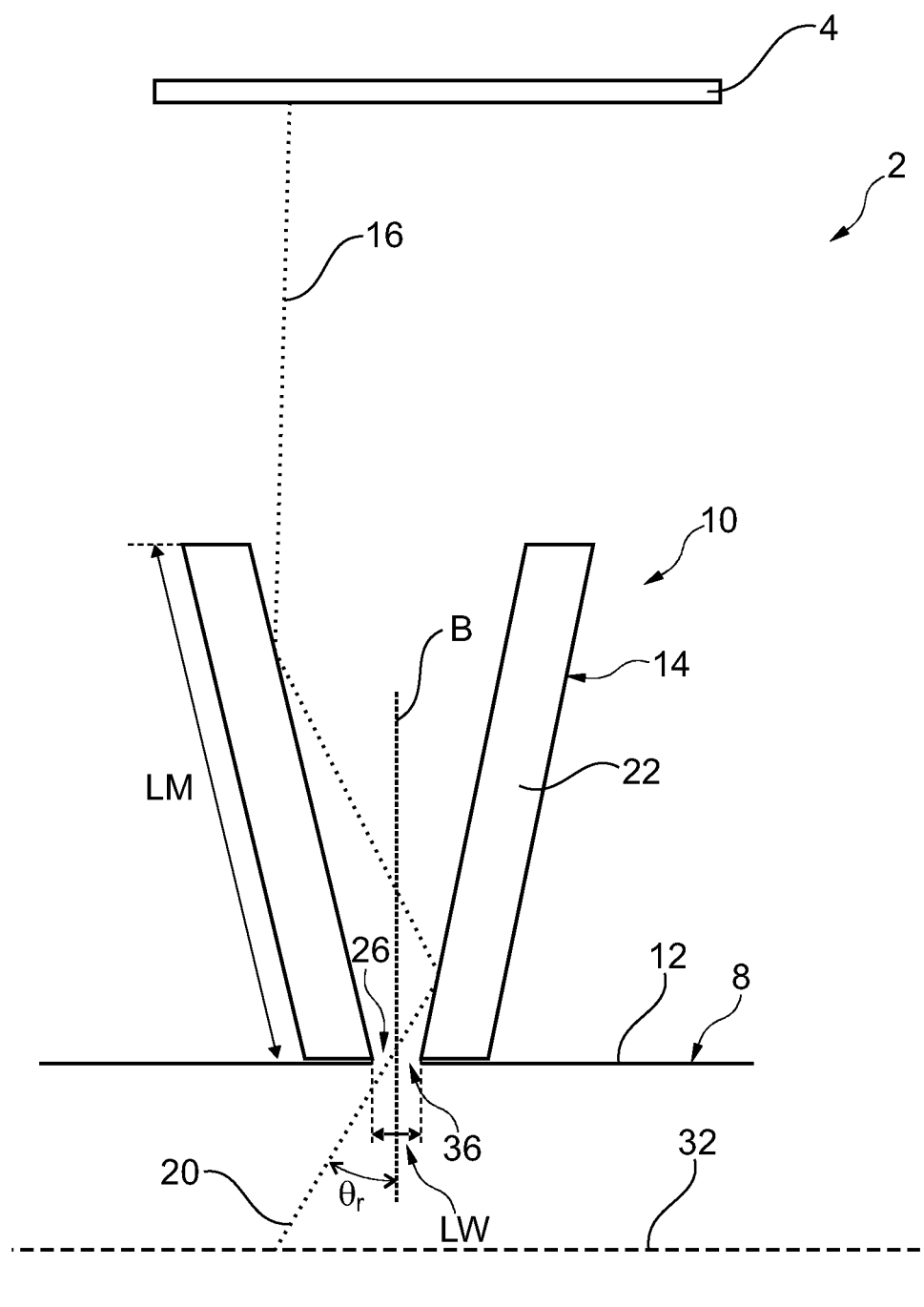
FIG. 5 shows a further example of an X-ray imaging apparatus.

According to a further example, as exemplary shown in FIG. 5, the set of mirrors 14 is arranged such that for the part 16 of X-ray radiation of the source 4 to be reflected at the set of mirrors 14, a maximum of one or two total reflections at the mirrors 22 of the set of mirrors 14 occur. Assuming that the exit width LW of the exit 26 of the set of mirrors 14 is given by a system design of the X-ray imaging apparatus 2 and that the angle of spread $\theta_m$ is given by a cone angle $\theta_k$ of the primary beam cone 28, it is preferred to adapt the length LM of each of the mirrors 22 of the set of mirrors 14 to limit the number of reflections at the mirrors 22 of the set of mirrors 14. Accordingly, it is preferred that the length LM of the mirrors 22 is adapted such that for the part 16 of the X-ray radiation to be totally reflected at at least one of the mirrors 22 of the set of mirrors 14 a maximum of one or two total reflections at the mirrors 22 of the set of mirrors 14 occur. By limiting the number of total reflections, the angle of reflection $\theta_r$ of the secondary X-ray radiation 29 (with respect to a common longitudinal axis A of the set of mirrors 14 and the aperture 36 of the pre-collimator 12) is limited. Limiting the angle of reflection $\theta_r$ of the secondary X-ray radiation 20, in particular with respect to the X-ray beams thereof, will limit the spot width KP of the secondary spot 38 and thus provides an increase in image quality of an object of interest.

Figure 6:
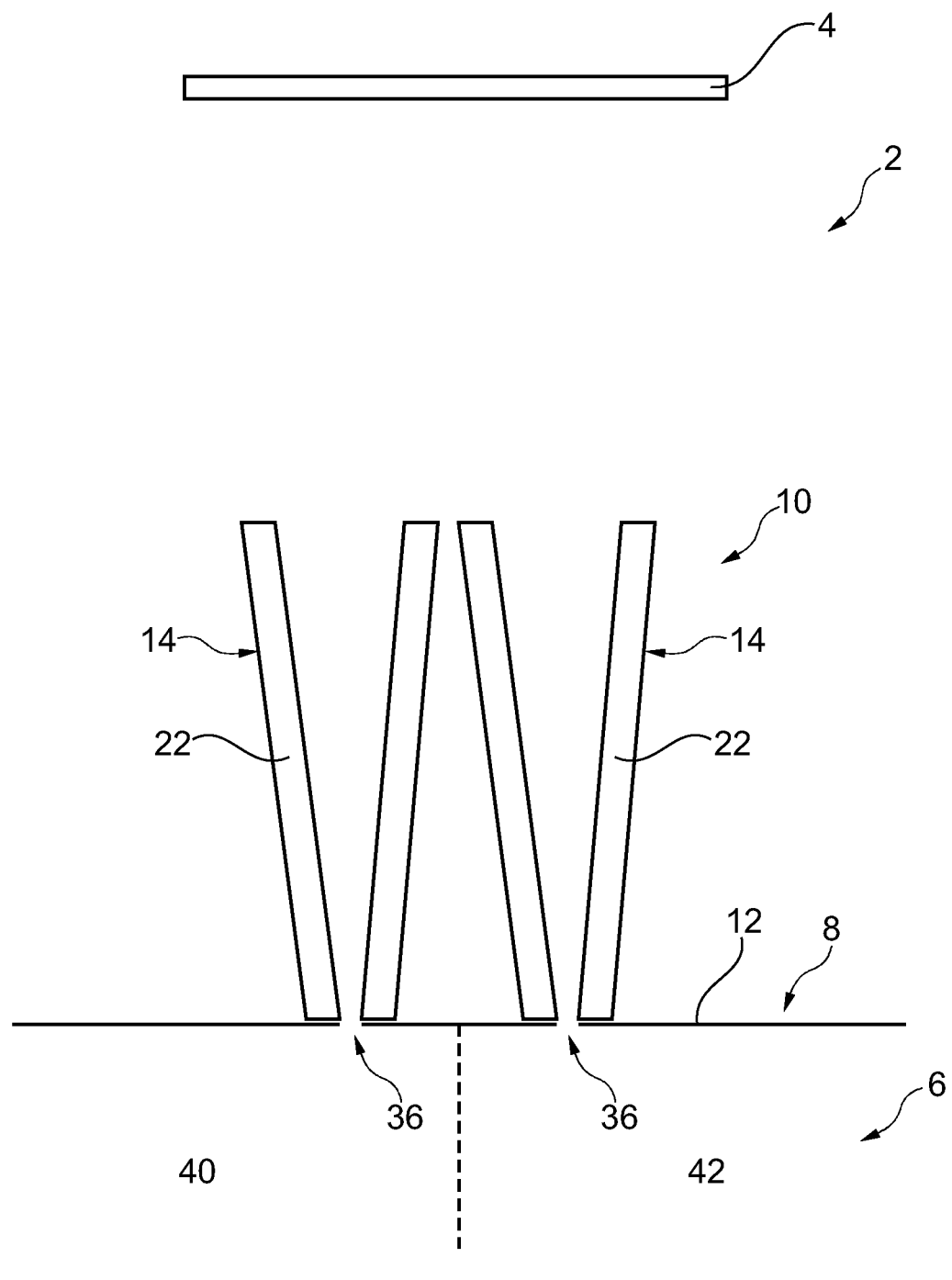
FIG. 6 shows a further example of an X-ray imaging apparatus.

According to a further example, as exemplary shown in FIG. 6, the pre-collimator 12 comprises at least two apertures 36, wherein, for each aperture 36 of the pre-collimator 12, the mirror arrangement 10 comprises an associated set of two mirrors 14. Accordingly, for each aperture 36 of the pre-collimator 12, a set of mirrors 14 is preferably provided, wherein the two mirrors 22 of each set of mirrors 14 is preferably formed as one of the set of mirrors 14 as exemplary described previously. The sets of mirrors 14 can be integrally formed. In particular, the set of mirrors are preferably made of the same means. In a further example, the mirrors of the set of mirrors are fasten together in order to form a rigidly fixed unit. This unit can be pre-build. A pre-collimator 12 comprising at least two apertures 36 allows providing enhanced X-ray radiation at two different areas 40, 42 in the object receiving space 6. Accordingly, this allows providing a first pair of a primary spot 34 and secondary spot 38 to be spaced apart from a further pair a primary spot 34 and a secondary spot 38. Thus, imaging can be performed in parallel at the two separated areas 40, 42. Parallel imaging reduces the total time for imaging an object of interest.

For example, two apertures 36 with an associated set of two mirrors 14 are provided as shown in FIG. 6. In further examples, more than two, e.g. three, four, five, six, seven, eight, nine or ten, or more than ten apertures 36 with a respective associated set of two mirrors 14 are provided. In an example, 15, 20, 25, 30 or more, or also numbers inbetween, apertures 36 are provided with associated sets of mirrors 14.

Figure 7:
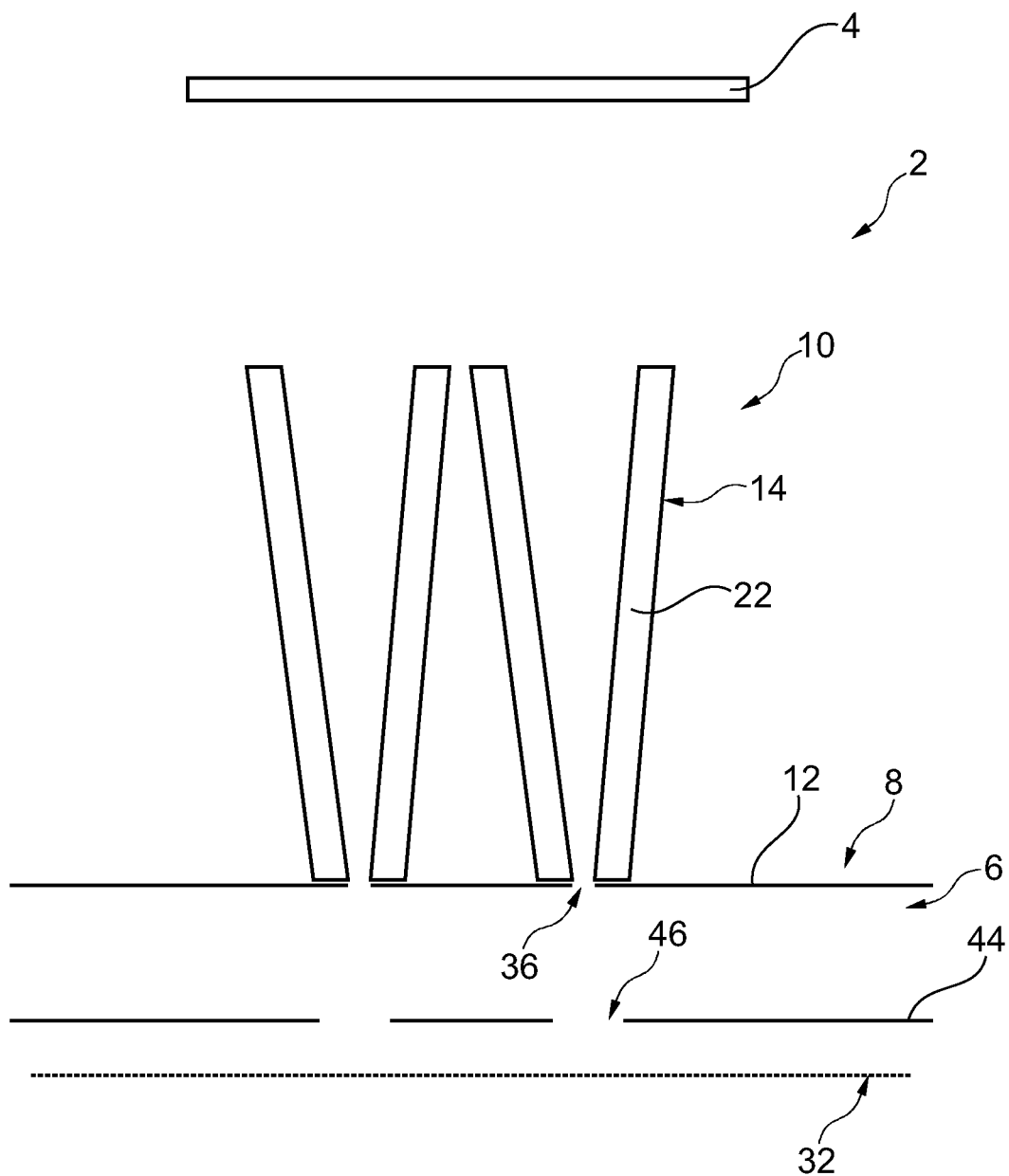
FIG. 7 shows a further example of an X-ray imaging apparatus.

According to a further example, as exemplary shown in FIG. 7, the collimator arrangement 10 of the X-ray imaging apparatus 2 comprises a post-collimator 44. Preferably, the object receiving space 6 is arranged between the pre-collimator 12 and the post-collimator 44. It is further preferred that the mirror arrangement 10 and the collimator arrangement 8 are arranged between the source 4 and the detector plane 32. Accordingly, X-ray radiation passing the mirror arrangement 10 and the collimator arrangement 8 is utilized for imaging an object of interest, which can be arranged in the object receiving space 6 between the pre-collimator 12 and the post-collimator 44 of the collimator arrangement 8. Preferably, the post-collimator 44 comprises at least one aperture 46. The at least one aperture 46 is preferably adapted for being passed by X-ray radiation. The remaining post-collimator 44 is preferably adapted for absorbing X-ray radiation. The at least one aperture 46 of the post-collimator 44 can be aligned with an aperture 36 of the pre-collimator with respect to a common longitudinal axis.

In a further example, the post-collimator 44 comprises at least two apertures 46. For each aperture 36 of the pre-collimator 12, the post-collimator 44 preferably comprises an associated aperture 46, in particular formed by one of the apertures 46 of the post-collimator 44.

In an example, an aperture 36 of the pre-collimator 12 and an aperture 46 of the post-collimator 44 are aligned with respect to a common axis, in particular to an optical axis intersecting the source 4, especially at its focal centre, such that the aperture 36 of the pre-collimator 12 and the aperture 46 of the post-collimator 44 are forming an aperture-pair of the collimator arrangement 8. The Collimator arrangement 8 preferably comprises at least two aperture-pairs. In a further example, each aperture 36, 46 of the collimator arrangement 8 is formed as a slit. Correspondingly, each aperture-pair can be formed as a slit-pair of the collimator arrangement 8.

Figure 8:
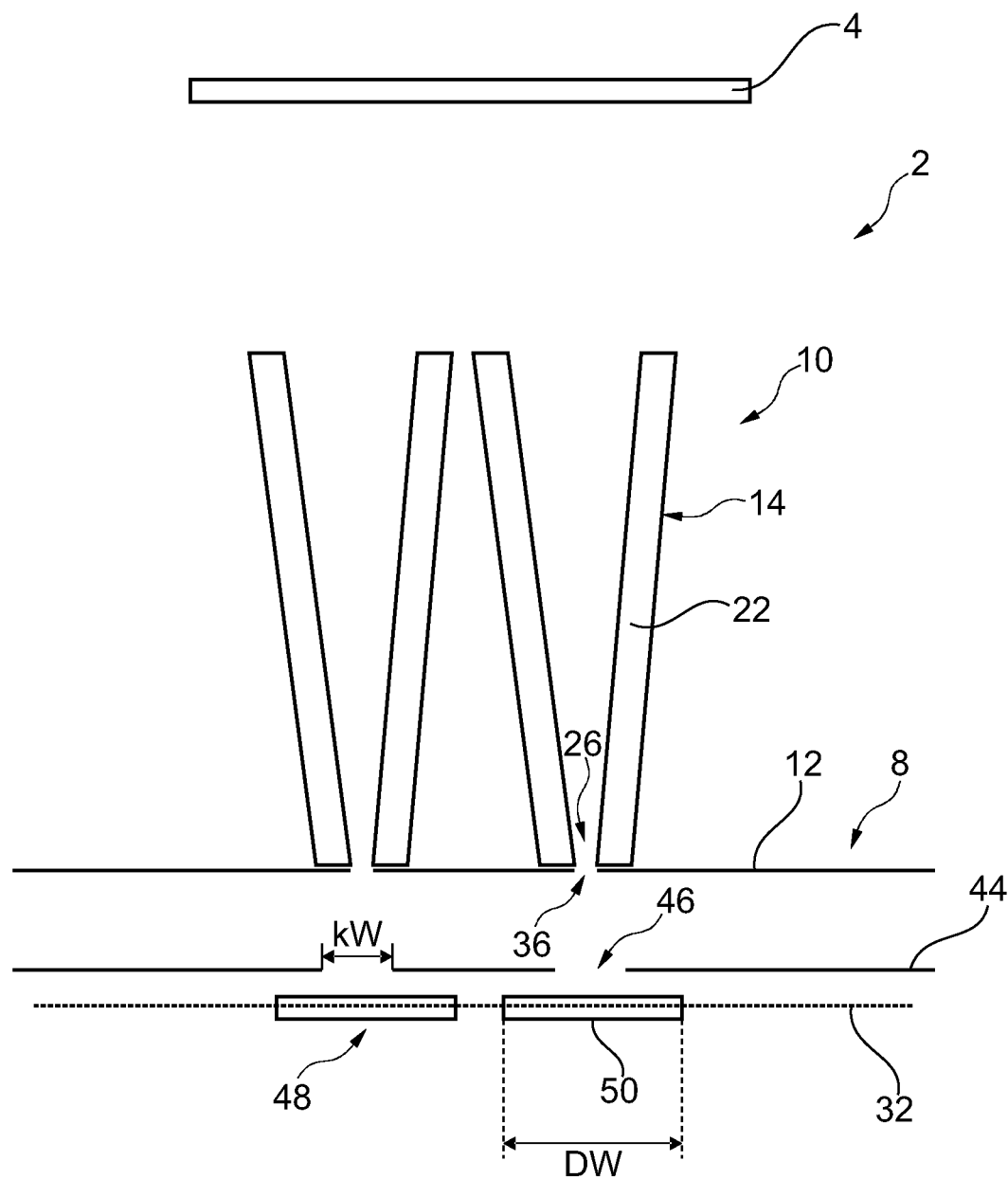
FIG. 8 shows a further example of an X-ray imaging apparatus.

According to a further example, exemplary shown in FIG. 8, the X-ray imaging apparatus 2 comprises a detector arrangement 48. Preferably, the detector arrangement 48 is arranged at the detector plane 32. Correspondingly, the mirror arrangement 10 and the collimator arrangement 8 are preferably arranged between the source 4 and the detector arrangement 48. The detector arrangement 48 comprises at least one detector 50. In an example, the detector 50, one of the at least one apertures 46 of the post-collimator 44, one of the at least one apertures 36 of the pre-collimator 12, and an exit 26 of a set of mirrors 14 are aligned with respect to a common longitudinal axis. The alignment is preferably with respect to an optical axis as the common axis intersecting the source 4, in particular its focus-centre. This provides a good imaging quality.

In an example, for each aperture 46 of the post-collimator 44 an associated detector 50 of the detector arrangement 48 is provided. Preferably, an aperture width KW of each aperture 46 of the post-collimator 44 is smaller than the detector width DW of the associated detector 50. Accordingly, each detector 50 is preferably adapted for detecting the X-ray radiation passing the associated aperture 46 of the post-collimator 44.

Figure 9:
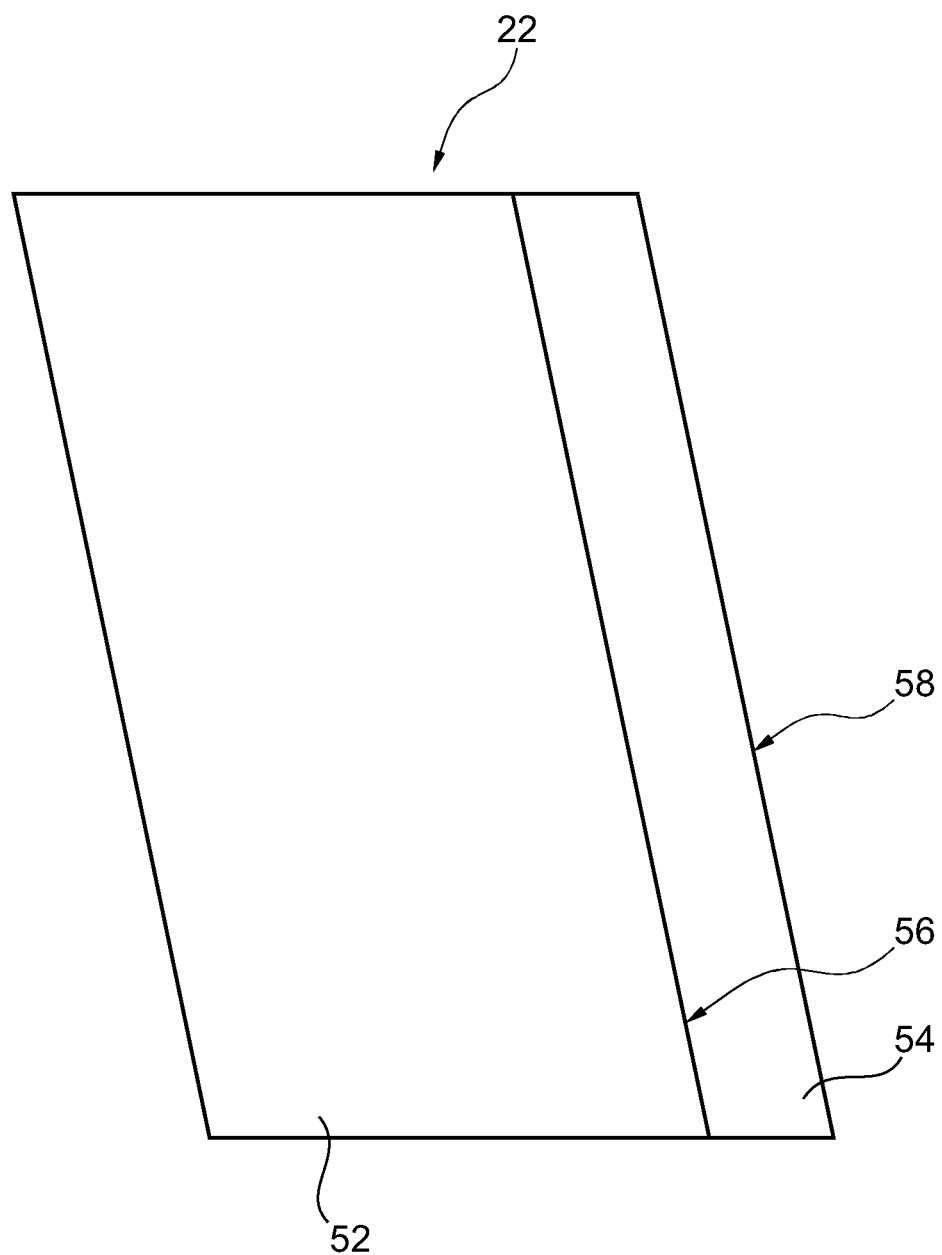
FIG. 9 shows an example of a part of a mirror of the set of mirrors in a schematic cross-section.

In FIG. 9, an example of the mirror 22 of the set of mirrors 14 is shown. The mirror 22 shown is exemplary for each of the two mirrors 22 of each set of mirrors 14.

In an example, each mirror 22 of the set of mirrors 14 comprises a substrate 52 with a coating layer 54 for providing total reflection, wherein, between the coating layer 54 and the substrate 52, a boundary 56 is provided, which is configured to reduce scatter radiation from an incoming radiation that is not reflected but passes a mirror surface 58 and enters the coating layer 54. Preferably, the density of the substrate 52 is higher than the density of the coating layer 54.

In an example, the boundary 56 is flat, in particular as flat as could be. However, in a further example, the boundary may have a roughness. Accordingly, it is hard to ensure that an angle of incidence $\theta_i$ is smaller than the critical angle $\theta_c$ for every wave of X-ray radiation impinging the boundary 46. At the boundary 46, the X-ray radiation may be totally reflected only at small fractions thereof. However, at very low incidence angles $\theta_i$ a microscopic roughness appears more and more flat. Therefore, in reality, a microscopic roughness will have only impact on the total reflection of the X-ray radiation for incident angles $\theta_i$ close to the critical angle $\theta_c$.

Figure 10:
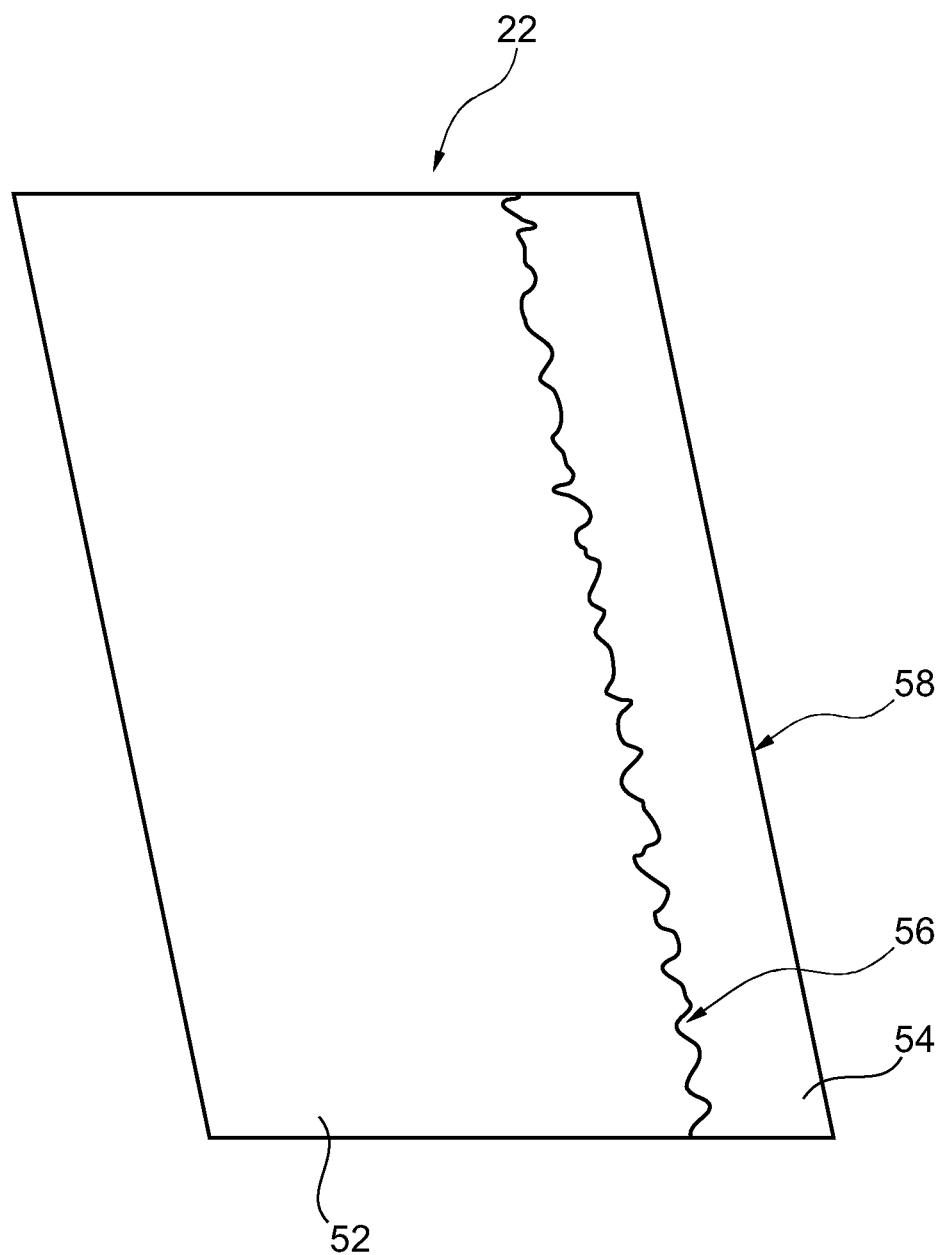
FIG. 10 shows another example of the mirror of the set of mirrors.

According to a further example, exemplary shown in FIG. 10, the boundary 56 has a randomly rough structured surface profile. In case an X-ray radiation beam is being reflected at the boundary 56, the randomly rough structured surface profile of the boundary 56 provides an effective beam reduction for suppressing reflected beam parts in such a way that the reflection conditions for the reflected beam parts are not fulfilled at the boundary 56. Accordingly, the reflected beam parts of the X-ray radiation are absorbed at the boundary 56 from the substrate 52 or the coating layer 54. As an effect thereof, a reduction of a scatter radiation from the incoming radiation when impinging at the boundary 56 is provided.

Figure 11:
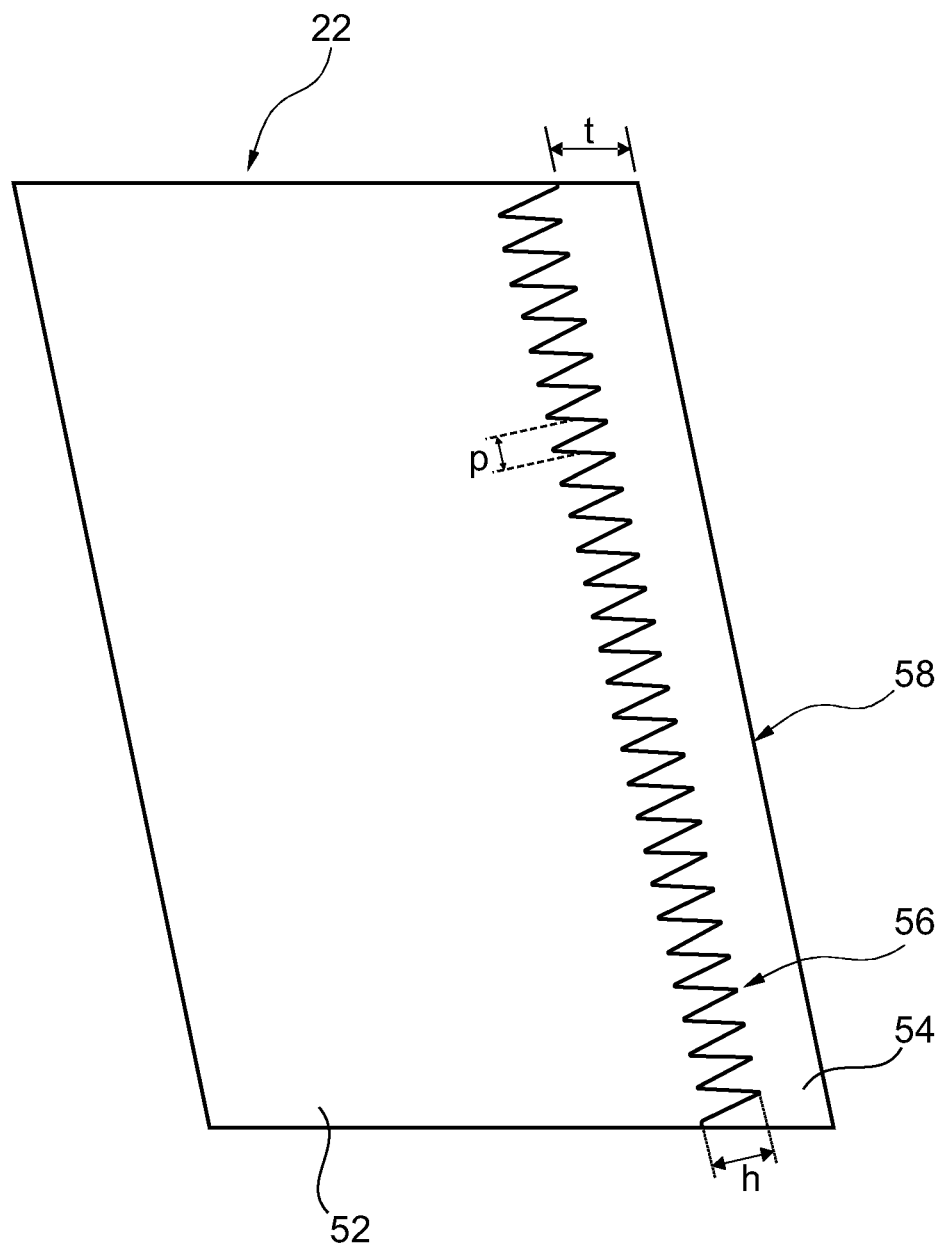
FIG. 11 shows a further example of the mirror of the set of mirrors.

An alternative configuration for the boundary 56 is exemplary shown in FIG. 11. According to an example, the boundary 56 has a periodical profile with a periodic height h between 0.05 mm (millimeter) and 1.5 mm, and a period p between 0.5 mm and 5 mm. The analogous effect as described previously with respect to the random rough surface applies for the periodical profile. Accordingly, analogue reference is made.

According to a further example, a thickness t of the coating layer is between 10 nm (nanometer) and 25 nm.

According to a further example, the coating layer comprises a material with an atomic number at the most of 9.

According to a further example (not further shown), between the coating layer 54 and the substrate 52, an uneven interface region is provided at the boundary 56. The interface region can be formed by the surfaces of the substrate 52 and the coating layer 54 facing each other.

According to an alternative example, the interface region is formed by a further layer, which is provided between the substrate 52 and the coating layer 54 and connecting the coating layer 54 with the substrate 52.

Figure 12:
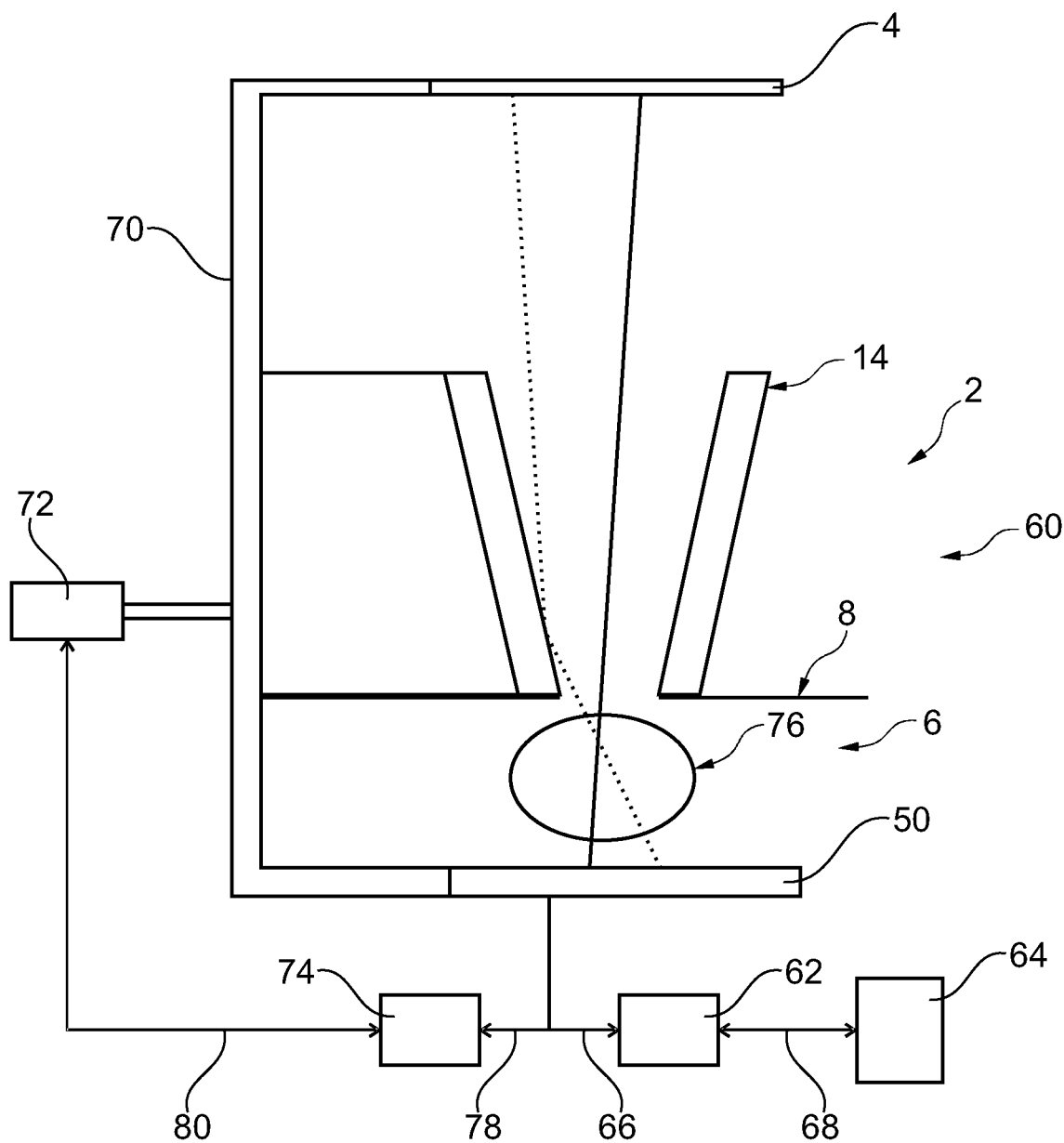
FIG. 12 shows a schematic setup of an example of an X-ray imaging system.

According to a further example, exemplary shown in FIG. 12, an X-ray imaging system 60 is provided. The imaging system 60 comprises an X-ray imaging apparatus 2 according to one of the previously examples, the detector 50 for detecting X-ray radiation passing the object receiving space 6 of the apparatus 2, and an imaging processing unit 62, as well as an imaging output unit 64. The imaging processing unit 62 is configured to receive signals from the detector 50 and to compute image data of an object of interest 76 arrangeable in the object receiving space 6 based on the signals, and the imaging output unit 64 is configured to provide an image data for further purpose.

Preferably, a signal connection 66 is provided, which connects the detector 50 with the imaging processing unit 62. Accordingly, the imaging processing unit 62 can obtain signals from the detector 50 via the signal line 66. A signal from the detector 50 preferably corresponds to detected X-ray radiation. The imaging processing unit 62 can be configured for processing the received signals from the detector 50 to compute an image in form of image data of an object of interest 76, which, when arranged in the object receiving space 6, can be applied with X-ray radiation from the source 4. The image data, which can be computed by the image processing unit 62, can be provided to the output unit 64. For transmitting the image data, a further signal line 68 can be provided for connecting the image processing unit 62 with the output unit 64. The output unit 64 is configured to provide the image data for further purpose. In an example, the output unit 64 can be a display or a monitor. In a further example, the output unit 64 can be configured to transmit the image data to a further unit (not shown).

In an example, the system 60 further comprises a mounting arrangement 70 for mechanically connecting the source 4, the mirror arrangement 14, the collimator arrangement 8 and the detector 50. Furthermore, an actuator 72 coupled to the mounting arrangement 70 to displace the mounting arrangement 70, and a control unit 74 to control the actuator 72 can be provided. The control unit 74 may be configured to receive signals from the detector 50 and to compute a control signal based on the received signals from the detector 50. In an example, the control unit 74 receives signals from the detector via a further signal line 78. Control signals from the control unit 74 can be sent to the actuator 72 via a further signal line 80. Preferably, the control unit 74 receives via a further signal line (not shown) signals from the source 4 or an associated controller.

In a further example, the control unit 74 controls the actuator 72 via the control signal sent to the actuator 72 and on the bases of the signals received. In particular, the control unit 74 controls the actuator 72 such that the mounting arrangement 70 is moved linearly or along a trajectory between a first position and a second position. As they are mechanically connected to the mounting arrangement 70, the source 4, the mirror arrangement 14, the collimator arrangement 8 and the detector 50 are moved correspondingly. Preferably, the object of interest 76 is held by a holder (not shown). The holder is not mechanically connected to mounting arrangement, such that the movement of the mounting arrangement will not apply to the holder. Accordingly, when the actuator 72 moves the mounting arrangement 70 and the elements mechanically connected to it, a relative movement is provided with respect to the holder and consequently to the object of interest 76. Accordingly, the object of interest 76 can be imaged at several different positions between the first position and the second position of the mounting arrangement 70, and thus being scanned. The control unit 74 can control the actuator 72 in open loop or in close loop. For the close loop control, a position sensor (not shown) for detecting the position of the detector 50 or the mounting arrangement 70 can be provided for the system 2. The detected position can be provided to the control unit 74 or the image processing unit 62. In case of scanning the object of interest 76, for each image taken a detected position can be associated. This allows computing a quasi continuous image of the object of interest 76.

In an example, the imaging processing unit 62 or the controller unit 74 can receive signals from the source 4 or an associated controller (not shown) for controlling the source 4, in order to control the X-ray radiation, in particular with respect to its intensity, emitted by the source 4.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those

The invention claimed is:

1. An X-ray imaging apparatus, comprising:
a source for generating X-ray radiation emitting a polychromatic spectrum of X-ray energies;
an object receiving space for arranging an object of interest for X-ray imaging;
an X-ray collimator arrangement; and
an X-ray mirror arrangement;
wherein the X-ray collimator arrangement comprises at least a pre-collimator arranged between the source and the object receiving space for providing collimated X-ray radiation to the object receiving space;
wherein the X-ray mirror arrangement is arranged between the source and the pre-collimator;
wherein the X-ray mirror arrangement comprises a set of two mirrors for guiding X-ray radiation of the source by providing total reflection of the whole polychromatic spectrum of X-ray energies of a part of the X-ray radiation in order to deflect the part of the X-ray radiation towards the pre-collimator such that in the region of the object receiving space enhanced radiation is provided in form of unreflected primary X-ray radiation in combination with secondary X-ray radiation by total reflection; and
wherein the mirrors of the set of two mirrors are facing one another with an angle of spread ($\theta m$) larger than zero, such that the set of mirrors providing an X-ray entrance having an entrance width and an X-ray exit having an exit width, which is smaller than the entrance width.

2. The apparatus according to claim 1, wherein the primary X-ray radiation forms a primary beam cone between the source and the pre-collimator,
wherein the mirrors of the set of mirrors abuts outside on the primary beam cone, and
wherein the angle of spread corresponds to a cone angle ($\theta k$) of the primary beam cone with a maximum deviation to the cone angle of 10%.

3. The apparatus according to claim 2, wherein a length LM of each of the mirrors of the set of mirrors is arranged, such that the inequality $$LM \leq LM\max = LW/(\Theta c2 - \Theta m)$$

holds, wherein:
LW is the width of the exit of the set of mirrors,
$\Theta c2$ is the critical angle of reflection at a mirror of the set of mirrors,
$\Theta m$ is the angle of spread of the mirrors of the set of mirrors.

4. The apparatus to claim 1, wherein the exit of the set of mirrors abuts to an aperture of the pre-collimator.

5. The apparatus according to claim 1, wherein the aperture of the pre-collimator is formed by the set of mirrors.

6. The apparatus according to claim 1, wherein the set of mirrors are arranged such that for the part of the X-ray radiation of the source to be reflected at the set of mirrors, a maximum of one or two total reflections at the mirrors of the set of mirrors occur.

7. The apparatus according to claim 1, wherein the pre-collimator comprises at least two apertures; and
wherein, for each aperture of the pre-collimator, the mirror arrangement comprises an associated set of mirrors.

8. The apparatus according to claim 1, wherein the collimator arrangement further comprises a post-collimator; and
wherein the object receiving space is arranged between the pre-collimator and the post collimator.

9. The apparatus according to claim 1, wherein each mirror of the sets of mirrors comprises a substrate with a coating layer for providing the total reflection; and
wherein, between the coating layer and the substrate, a boundary is provided that is configured to reduce scatter radiation from incoming radiation that is not reflected but passes a mirror surface and enters the coating layer.

10. The apparatus according to claim 9, wherein, between the coating layer and the substrate, an uneven interface region is provided as the boundary.

11. The apparatus according to claim 10, wherein the interface has a randomly rough structured surface profile.

12. The apparatus according to claim 10, wherein the interface has a periodical profile with a periodical height between 0.05 mm and 1.5 mm, and a period between 0.5 mm and 5 mm.

13. The apparatus according to claim 12, wherein a thickness of the coating layer is between 10 nm and 25 nm.

14. An X-ray imaging system, comprising:
an apparatus comprising:
a source for generating X-ray radiation emitting a polychromatic spectrum of X-ray energies;
an object receiving space for arranging an object of interest for X-ray imaging;
an X-ray collimator arrangement; and
an X-ray mirror arrangement;
wherein the X-ray collimator arrangement comprises at least a pre-collimator arranged between the source and the object receiving space for providing collimated X-ray radiation to the object receiving space;
wherein the X-ray mirror arrangement is arranged between the source and the pre-collimator;
wherein the X-ray mirror arrangement comprises a set of two mirrors for guiding X-ray radiation of the source by providing total reflection of the whole polychromatic spectrum of X-ray energies of a part of the X-ray radiation in order to deflect the part of the X-ray radiation towards the pre-collimator such that in the region of the object receiving space enhanced radiation is provided in form of unreflected primary X-ray radiation in combination with secondary X-ray radiation by total reflection; and
wherein the mirrors of the set of two mirrors are facing one another with an angle of spread ($\theta m$) larger than zero, such that the set of mirrors providing an X-ray entrance having an entrance width and an X-ray exit having an exit width, which is smaller than the entrance width;
a detector for detecting X-ray radiation passing the object receiving space;
an imaging processing unit; and
an image data output unit;

wherein the imaging processing unit is configured to receive signals from the detector; and to compute image data of an object based on the signals; and wherein the image data output unit is configured to provide the image data for further purpose.

15. An X-ray imaging system according to claim 14, further comprising:

a mounting arrangement for mechanically connecting the source, the mirror arrangement, the collimator arrangement and the detector, an actuator coupled to the mounting arrangement to displace the mounting arrangement, and a control unit to control the actuator, wherein the control unit is configured to receive signals from the detector and to compute a control signal based on the received signals from the detector.

* * * * *